United States Patent [19]
Bisset et al.

[11] 3,986,976
[45] Oct. 19, 1976

[54] KETONE PEROXIDE COMPOSITIONS

[75] Inventors: Douglas M. Bisset, Sarnia; Colin Mercer, Port Lambton, both of Canada

[73] Assignee: Chinook Chemicals Corporation Limited, Sombra, Canada

[22] Filed: Feb. 7, 1975

[21] Appl. No.: 547,795

Related U.S. Application Data

[62] Division of Ser. No. 396,524, Sept. 12, 1973, Pat. No. 3,957,884.

[52] U.S. Cl. ............................ 252/186; 260/610 R; 260/610 A
[51] Int. Cl.² ...................................... C07C 179/00
[58] Field of Search ................. 252/186; 260/610 R, 260/610 A

[56] References Cited
UNITED STATES PATENTS

| | | | |
|---|---|---|---|
| 3,330,871 | 7/1967 | Mageli et al. | 260/610 A |
| 3,507,800 | 4/1970 | Leveskis | 252/186 |
| 3,649,548 | 3/1972 | McCloskey et al. | 252/186 |
| 3,692,841 | 9/1972 | McCloskey et al. | 260/610 R |
| 3,702,869 | 11/1972 | Leveskis et al. | 260/610 A |

*Primary Examiner*—Benjamin R. Padgett
*Assistant Examiner*—Irwin Gluck
*Attorney, Agent, or Firm*—Sim & McBurney

[57] ABSTRACT

Safe ketone peroxide compositions are provided utilizing a novel solvent system which boils smoothly over a wide range of temperatures.

8 Claims, 1 Drawing Figure

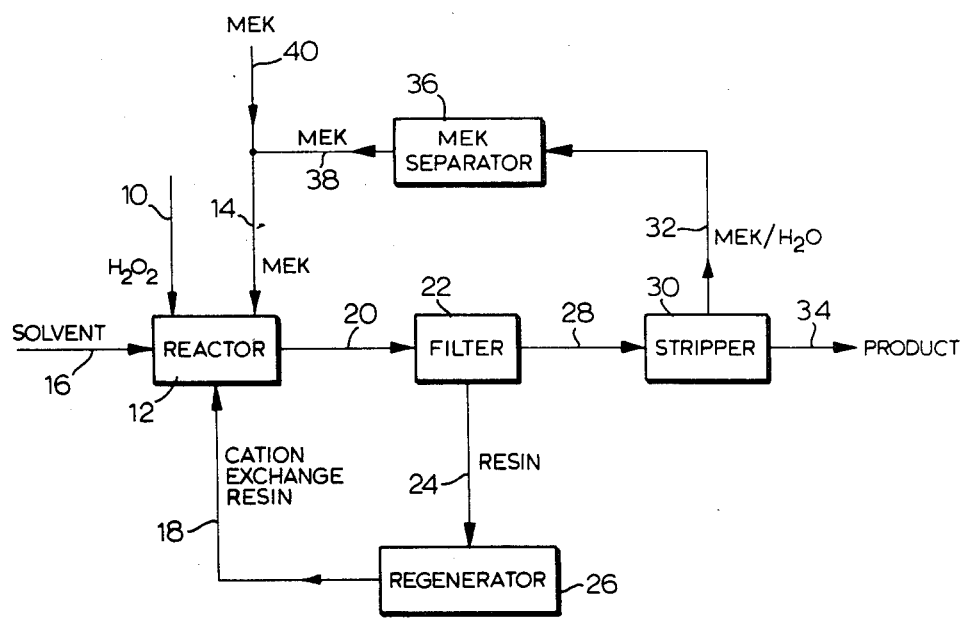

KETONE PEROXIDE COMPOSITIONS

REFERENCE TO RELATED APPLICATIONS

This application is a division of application Ser. No. 396,524 filed Sept. 12, 1973 (now U.S. Pat. No. 3,957,884).

FIELD OF INVENTION

The present invention is directed to ketone peroxide compositions, particularly "safe" ketone peroxide compositions.

BACKGROUND TO THE INVENTION

Ketone peroxides are extensively used for the initiation of polymerization of ethylenically unsaturated compounds. Peroxides, however, have a tendency to be inflammable and explosive, with some exhibiting these properties to a greater extent than others. These properties carry with them obvious hazards to the users of the materials as well as to the manufacturers.

Many suggestions have been made to reduce the inflammability of ketone peroxides usually involving the incorporation of large quantities of water in the composition, the use of various additives and the use of particular solvents.

One typical prior art suggestion to provide safe ketone compositions is described in U.S. Pat. No. 3,330,871, wherein it is indicated that a class of "Safety Solvents" for for ketone peroxide may be used to provide compositions which exhibit resistance to ignition and once ignited burn mildly. A wide variety of solvents is mentioned including various glycols. However, it has been found that, while the compositions provided in the manner disclosed in this patent do indeed exhibit some resistance to ignition and once ignited burn mildly, after burning for a period of time, which may vary widely depending on the solvent used and the quantity present, the composition suddenly flares up and burns vigourously. The tendency of these prior art compositions to flare up suddenly is extremely hazardous to a user or manufacturer seeking to extinguish the ignited composition, since while the ignited composition may be burning mildly and the operator can approach the flame with suitable extinguishing equipment, before extinguishing the flame, a sudden flare up may occur, causing injury to the operator.

SUMMARY AND GENERAL DESCRIPTION OF INVENTION

The present invention provides a safe acyclic ketone peroxide composition which exhibits considerable resistance to ignition and when ignited burns in a controlled manner until all the peroxide composition has been consumed. Thus, the present invention avoids the flare up problem attendant the prior art compositions of U.S. Pat. No. 3,330,871.

In accordance with the present invention a composition is provided which is a homogeneous solution of the acyclic ketone peroxide in a solvent system, the solution having a flash point of at least about 200° F. The solvent system and the individual solvents thereof essentially conform to several characteristics:

i. a mixture of solvents which boils smoothly over a wide range of temperatures, preferably at least 40° C and which commences to boil at a temperature of at least 175° C, the individual solvents having differing boiling points, preferably between about 200° and 300° C;

ii. a mixture of solvents which has a flash point of at least 200° F, preferably at least 220° F;

iii. a mixture of solvents which has an auto-ignition temperature of at least 225° C, preferably about 300° to 1000° C;

iv. a mixture of solvents which is a solvent for the ketone peroxide, water and free ketone, and additionally is compatible with the polymer system to be formed;

v. a mixture of solvents having low volatility;

vi. a mixture of solvents inert to the ketone and hydrogen peroxide reactants and product peroxide;

vii. a mixture of solvents which has a low toxicity;

viii. a mixture of solvents which does not leave a solid residue after burning, which otherwise would result in afterglow;

ix. the individual solvents must be non-benzenoid;

x. the individual solvents must contain from 2 to 8 acyclic carbon atoms;

xi. the individual solvents should be inert and incapable of degradation under conditions of formation of the product to materials which may decompose the product peroxide;

xii. the individual solvents must be non-halogenated, and xiii. the individual solvents should be incapable of forming amine oxides.

Autoignition temperatures for various solvents and the determination thereof are described in an article entitled "Autoignition Temperatures of Organic Chemicals" by Carlos J. Hilads et al., Chemical Engineering, Sept. 4, 1972, pp 75 to 80. Autoignition is the lowest temperature at which a material begins to self-heat at a high enough rate to result in combustion.

By utilizing a mixture of solvents of differing boiling points and which boils smoothly over a wide temperature range, the heat of decomposition of the peroxide is used as heat of vaporization of the solvents and hence flare up due to decomposition of the aliphatic ketone peroxide is not possible.

The ketone peroxide composition provided in accordance with this invention has been found to have excellent end use properties. For example, in spray coat applications where polyester gels of only a few thousandths of an inch thick, typically 10 to 15000, are provided, the product of the invention does not give rise to blisters or pin holes, in contrast to many commercially-available ketone peroxide formulations.

Additionally, it has been found that where tapered sections or sections of irregular thickness are cured from curable polyester materials in which the ketone peroxide composition of this invention is used as the polymerization initiator, this curing takes place uniformly throughout the thickness of the film. This result is of importance in particular in the fabrication of boats where the use of uneven thickness of polyester film is common.

As a result of this unexpected uniformity of curing, there is less laminate stress and lack of excessive localised heat build up. The stresses and heat build up can cause damage to the expensive molds used in the boat industry and hence should be avoided. In addition, bubbling caused by solvents is not observed in the polyester films.

A further result achieved in film formation initiated with the compositions of the invention is that when the cured article, such as a boat, is removed from the mold, the film is completely cured. In many conventional systems, the film is not completely cured upon removal from the mold.

Compositions in accordance with the present invention have improved solubility in diallyl phthalate, as compared to conventional commercially-available fire retardent ketone peroxide compositions. This property is important since diallyl phthalate is widely used as a cross-linking diluent in spray applications of ketone peroxides.

The acyclic ketone peroxide present in the compositions of the present invention is derived from an acyclic ketone of the formula R—CO—R', where R and R' each are straight or branched chain alkyl groups in which the total number of carbon atoms in R and R' is from 3 to 6.

Suitble ketones include diethyl ketone, methyl ethyl ketone (MEK), methyl propyl ketone and methyl isobutyl ketone.

The ketone most commonly employed to form ketone peroxides is methyl ethyl ketone and this particular material is preferred in the present invention. The invention will be described hereinafter with particular reference to this ketone.

The compositions of the present invention may be prepared in any convenient manner, preferably that described in the parent application Ser. No. 396,524. In this procedure, which is described in more detail in the parent application, a stoichiometric excess of an acyclic ketone is reacted with hydrogen peroxide in a homogeneous system provided by the solvent system mentioned above. The resulting homogeneous solution is boiled under reduced pressure to strip excess ketone and water from the solution to provide the desired product.

BRIEF DESCRIPTION OF DRAWING

The sole FIGURE of the drawing shows a schematic flow sheet of a procedure for the formation of the compositions of this invention.

DESCRIPTION OF PREFERRED EMBODIMENT

Referring to the drawing, which depicts the formation of ketone peroxide compositions by the procedure of the parent application Ser. No. 396,524, hydrogen peroxide, typically as an aqueous solution thereof containing 50 percent $H_2O_2$, is fed by line 10 to a reactor 12 containing methyl ethyl ketone fed by line 14 and solvent fed by line 16. A cation exchange resin in hydrogen ion form, fed by line 18 generally in the form of beads and insoluble in the reactants or the solvent, also is present in the reactor 12. The hydrogen peroxide generally is added dropwise to the solution to react with the methyl ethyl ketone and the reaction may be continued after completion of addition of the hydrogen peroxide.

The quantity of methyl ethyl ketone fed by line 14 is at least 1.1 times the stoichiometric quantity required to react with the hydrogen peroxide fed by line 10. Typically the amount is at least 1.5 times the weight of the hydrogen peroxide solution fed by line 10.

The solvent fed by line 16 is one conforming to the requirements of the solvent system as outlined above. Each of the solvents may contain from 2 to 8 acyclic carbon atoms.

Typical mixtures which may be used to provide the solvent system, especially with methyl ethyl ketone peroxide, include various mixtures of C2 to C6 glycols and C3 to C6 trialkyl phosphates, for example, mixtures of numbers of the following materials:

|  | Boiling Point ° C. | Flast Point ° F. |
|---|---|---|
| Ethylene Glycol | 197.2 | 240.8 |
| Diethylene Glycol | 245.0 | 290 |
| Dipropylene Glycol | 233 | 330 |
| Hexylene Glycol | 198 | 230 |
| Triethyl phosphate | 216 | 240 |

Crude ethylene glycol, usually containing quantities of diethylene glycol and triethylene glycol, may be used in the solvent system fed by line 16. Glycol derivatives, such as ethylene glycol acetate, may be used in the solvent system.

The relative proportions of the solvents, their number, and the difference between their individual boiling points in the solvent system may vary widely and are a matter of choice, provided that the overall composition and the individual components conform to the above-described parameters.

The quantity of solvent fed by line 16 should be at least sufficient to maintain a homogeneous reaction mixture throughout the addition of hydrogen peroxide.

The reaction is carried out at as low a temperature as possible compatible with speed of reaction. Higher temperatures favour decomposition of the product, whereas low temperatures below 10° C result in long reaction times. The process is carried out at a temperature below about 35° C, preferably between about 20° to 30° C, with reaction times from about 1 to 2 hours.

Following completion of the reaction of the hydrogen peroxide with the methyl ethyl ketone there is obtained a homogeneous solution of solvent, product ketone peroxide, water and unreacted methyl ethyl ketone in admixture with resin. The admixture is passed by line 20 to a filter 22 wherein the solid resin is filtered from the homogeneous solution. Alternatively, the resin may be separated after the next processing step.

The recovered resin is passed by line 24 to a regenerator 26 prior to recycle of regenerated cation exchange resin to the reactor 12 by line 18.

The filtered solution then is passed by line 28 to a stripper 30 wherein the solution is heated under reduced pressure to remove an azeotrope of methyl ethyl ketone and water. While three separate units, namely reactor 12, filter 22 and stripper 30 are described, this is for ease of illustration of the process of the invention, and the three operations may be carried out in a single vessel.

The stripper 30 generally is maintained under a vacuum in order to lower the stripping temperature and hence reduce the danger of decomposition of the ketone peroxide. The temperature of operation of the stripper 30 generally is less than about 40° C with the applied vacuum being as high as possible. The excess methyl ethyl ketone and water are removed from the homogeneous system in the stripper 30 by line 32. The stripping usually is continued until no further material can be stripped from the product, and usually is complete in less than 4 hours, usually about 1 hour.

The resulting solution of methyl ethyl ketone peroxide in solvent in line 34 is substantially free from unreacted methyl ethyl ketone and free water.

It is preferred to provide in the resulting solution of methyl ethyl ketone in solvent in line 34 a water content less than about 5 percent, preferably from 0 to about 4 percent. The water content of the product may be determined readily by gas chromatographic techniques. This technique also may be used to determine the free ketone content of the product which preferably, is as low as possible. The free ketone concentrations of the product should be below a value which will substantially lower the flash point of the product, usually below about 0.5 percent and, preferably, from 0 to about 0.4 percent.

The product containing the preferred water content conforms to the so-called "Freezing Test". In the Freezing Test, the product is cooled to −50° C and then thawed. To pass this test, the product must remain mobile on lowering the temperature to −50° C and homogeneous on thawing.

When a conventional aliphatic ketone peroxide composition containing substantial quantities of water is cooled and subsequently thawed, freezing occurs on lowering the temperature, and a phase separation occurs on thawing which is extremely difficult to reverse and, additionally, following such phase separation, the composition becomes more susceptible to explosion.

Further, it has been observed that upon subjecting commercially-available peroxide compositions of low water content to the Freezing Test, the products solidified between 0° and −5° C.

The product in line 34 has been found to have improved stability properties as compared to conventionally-produced ketone peroxide compositions, thereby providing a product which may be stored over long periods without substantial loss of activity and danger of instability if stored through cold weather.

The concentration of the ketone peroxide in the product in line 34 may be in excess of the industry standard of 11 percent active oxygen, in which case the product may be diluted with further amounts of solvent, either during the stripping operation or thereafter, to provide the required active oxygen value.

The active oxygen content of the final composition may vary widely, typically from 0.1 to 13 percent AO, with varying quantities of solvent being employed, typically from 5 to 90 percent of the composition.

The material in line 32 may be passed to a separator 36 wherein the methyl ethyl ketone is separated and forwarded by line 38 to mix with further methyl ethyl ketone fed by line 40 to provide the methyl ethyl ketone feed in line 14.

By utilizing an excess of methyl ethyl ketone there is realized an economic utilization of hydrogen peroxide, and since the excess is recovered for recycling, hence, there is also economic utilization of ketone.

EXAMPLES

The invention is illustrated further by the following Examples:

EXAMPLE I

A mixture of solvents consisting of 7.38 lbs of triethyl phosphate, 2.62 lbs of ethylene glycol, 2.62 lbs of diethylene glycol and 2.62 lbs of dipropylene glycol was charged to a reaction vessel and 66.5 lbs of methyl ethyl ketone was added. 1.36 lbs of Dowex 50 W - X8 cation exchange resin in hydrogen ion form was added to the solution in the reaction vessel.

The mixture of solvents charged to the reaction vessel was found to commence boiling at 179.5° C and to boil smoothly to dryness over an increasing temperature range to 224.0° C.

41.6 lbs of 50 percent aqueous solution of hydrogen peroxide was added slowly with stirring over a 45 minute period, with the temperature being controlled by cooling below about 88° F. The resulting mixture was allowed to react, with stirring and agitation by nitrogen gas bubbled through, for a further 75 minutes.

The liquid in the reaction vessel remained homogeneous throughout the reaction and then was cooled to ambient temperature prior to filtration of the cation exchange resin therefrom.

Under a vacuum of approximately 27 inches mercury, the filtrate was stripped of water and unreacted methyl ethyl ketone over a period of about 3½ hours at a rising temperature between 70° and 116° F.

41.2 lbs of stripped material was recovered and 70 lbs of methyl ethyl ketone peroxide solution was obtained. The product was very difficult to ignite, and when ignited burned with a controlled flame until all the liquid was consumed.

In addition, the product was subjected to the Freeze Test and the liquid remained mobile on cooling to −50° C and did not exhibit phase separation on cooling and thawing.

The product had an active oxygen content of about 11.5 percent and samples after storage for 183 days under laboratory conditions in which the temperature ranged from 50° to 95° F, mainly 65° to 75° F exhibited an active oxygen content of 11.2 percent, thereby indicating the stability of the product.

In similar storage tests when exposed to outdoor weather conditions in which the temperature ranged from −5° F to 80° F (shade temperature), the active oxygen content of the product after 148 days was 7.4 percent, while comparative samples of Aposet 720 and FR222 had exploded by that time.

EXAMPLE II

A two-gram sample of the product of Example I was placed in a small aluminum dish 12.5 mm high by 44 mm diameter. Similar two-gram samples of commercially-available peroxide compositions known as DNF (Wallace and Tiernan and formulated in accordance with U.S. Pat. No. 3,330,871) and Aposet 720 (M and T) were placed in similar dishes.

A ¾ inch flame from a small pilot burner was adjusted to impinge the liquid surface at about a 60° angle. The flame was removed on ignition of the sample. The times to ignition were recorded for a number of samples and the average times are reproduced in the Table I:

TABLE I

| | |
|---|---|
| Example 1 | 71 secs. |
| DNF | 68 secs. |
| Aposet 720 | 25 secs. |

Total burning times varied within samples of each product and a true comparison in this regard was not possible. The product of Example I burned mildly until all the peroxide had been consumed. On the other hand the DNF burned mildly for a short time before burning very vigorously.

A sample product formed from methyl ethyl ketone and hydrogen peroxide in ethylene glycol burned very readily.

Modifications are possible within the scope of the invention.

What we claim is:

1. An acyclic ketone peroxide composition having an active oxygen content of about 0.1 to about 13 percent and a flash point of at least about 200° F and consisting essentially of a homogeneous solution of 10 to 95 percent of (a) an acyclic ketone peroxide derived from an acyclic ketone of the formula R—CO—R' where R and R' each are straight or branched chain alkyl groups in which the total number of carbon atoms is from 3 to 6, in 90 to 5 percent of (b) a solvent system consisting of a mixture of solvents which boils smoothly over a wide range of temperatures and which commences to boil at a temperature of at least 175° C, having a flash point of at least 200° F and an autoignition temperature of at least 225° C, said mixture having a low volatility, low toxicity and being a solvent for and inert to the ketone peroxide, said mixture of solvents being incapable of leaving a solid residue after burning, the individual solvents of said mixture being non-benzenoid, non-halogenated and incapable of forming amine oxides, said individual solvents being selected from C2 to C6 glycols and C3 to C6 trialkyl phosphates and having differing boiling points, said solution containing 0 to about 0.5 percent of free acyclic ketone and 0 to about 5 percent of water.

2. The composition of claim 1 having an active oxygen content of about 11 percent.

3. The composition of claim 1 wherein said acyclic ketone peroxide is methyl ethyl ketone peroxide.

4. The composition of claim 1 wherein said solvent system boils smoothly over an at least 40° C temperature range.

5. The composition of claim 1 wherein said mixture has a flash point of at least 220° F.

6. The composition of claim 1 wherein said mixture has an autoignition temperature of about 300° to 1000° C.

7. The composition of claim 1 wherein said individual solvents are selected from ethylene glycol, diethylene glycol, dipropylene glycol, hexylene glycol and triethyl phosphate.

8. The composition of claim 1 wherein said individual solvents have differing boiling points between about 200° and about 300° C.

* * * * *